United States Patent
Glanznig et al.

(10) Patent No.: US 10,837,950 B2
(45) Date of Patent: Nov. 17, 2020

(54) METHOD AND DEVICE FOR DETERMINING LOW TEMPERATURE PROPERTIES

(71) Applicant: GRABNER INSTRUMENTS MESSTECHNIK GMBH, Vienna (AT)

(72) Inventors: Gerd Glanznig, Vienna (AT); Josef Lutz, Rohrau (AT)

(73) Assignee: GRABNER INSTRUMENTS MESSTECHNIK GMBH, Vienna (AT)

( * ) Notice: Subject to any disclaimer, the term of this patent is extended or adjusted under 35 U.S.C. 154(b) by 231 days.

(21) Appl. No.: 15/761,142

(22) PCT Filed: Sep. 22, 2016

(86) PCT No.: PCT/AT2016/000084
§ 371 (c)(1),
(2) Date: Mar. 19, 2018

(87) PCT Pub. No.: WO2017/054019
PCT Pub. Date: Apr. 6, 2017

(65) Prior Publication Data
US 2018/0267009 A1    Sep. 20, 2018

(30) Foreign Application Priority Data
Sep. 29, 2015    (AT) .................................. A 636/2015

(51) Int. Cl.
*G01N 25/00*    (2006.01)
*G01N 33/28*    (2006.01)
(Continued)

(52) U.S. Cl.
CPC ......... *G01N 33/2811* (2013.01); *G01N 11/08* (2013.01); *G01N 25/04* (2013.01)

(58) Field of Classification Search
CPC .... G01N 33/00; G01N 33/28; G01N 33/2823; G01N 33/2829; G01N 33/2888;
(Continued)

(56) References Cited

U.S. PATENT DOCUMENTS 3,122,911 A    3/1964    Conklin
3,213,668 A    10/1965    Thompson
(Continued)

FOREIGN PATENT DOCUMENTS

DE    2701276 A1    7/1977
DE    2634474 A1    9/1977
(Continued)

OTHER PUBLICATIONS

International Search Report PCT/AT2016/000084 dated Dec. 21, 2016 w/English translation.
(Continued)

*Primary Examiner* — Gail Kaplan Verbitsky
(74) *Attorney, Agent, or Firm* — Pillsbury Winthrop Shaw Pittman, LLP

(57) ABSTRACT

In a method for determining the low-temperature properties of a paraffin-containing fuel, the fuel is conducted from a storage chamber through a measuring cell provided with a sieve, the measuring cell is cooled by means of a cooling device, the temperature of the fuel in the measuring cell is measured, and a fluid pressure representing the flow resistance occurring on the sieve is measured, and the temperature occurring at a defined fluid pressure set point is determined and output as a result of the method, wherein, for the pressure measurement, a defined sample amount of the fuel is abruptly delivered from the storage chamber in order to obtain a pressure pulse.

27 Claims, 1 Drawing Sheet

(51) Int. Cl.
*G01N 11/08* (2006.01)
*G01N 25/04* (2006.01)

(58) Field of Classification Search
CPC .. G01N 25/00; G01N 25/68; G01N 2011/002; G01N 1/2247; G01N 25/04; G01N 25/14; G01N 25/147; G01N 27/02; G01N 33/2811; G01N 25/62; F02D 19/0628; F02D 2200/0602; F02D 2200/0606; F02D 2200/0611; G01K 11/06; G01K 1/12
USPC .. 374/4, 5, 141, 143, 16, 28, 10, 45, 30–39, 374/24
See application file for complete search history.

(56) References Cited

U.S. PATENT DOCUMENTS

| | | | |
|---|---|---|---|
| 3,872,710 A | 3/1975 | Louvel | |
| 4,023,397 A | 5/1977 | Ouvrard | |
| 4,292,837 A * | 10/1981 | Oakman | F25B 25/00 374/24 |
| 5,046,355 A | 9/1991 | Tack et al. | |
| 6,035,706 A * | 3/2000 | Campagnolo | G01N 33/2811 374/23 |
| 7,833,488 B2 * | 11/2010 | Karlsson | B01D 9/005 422/528 |
| 8,034,304 B2 * | 10/2011 | Karlsson | G01N 31/10 422/501 |
| 8,268,629 B2 * | 9/2012 | Coleman | G01N 33/2847 422/82.01 |
| 2009/0283068 A1 * | 11/2009 | Willison | F02M 37/22 123/27 R |
| 2011/0083994 A1 | 4/2011 | Sirota et al. | |
| 2012/0192480 A1 * | 8/2012 | Barrett | C10L 3/00 44/300 |
| 2014/0142270 A1 * | 5/2014 | Maehling | C08F 8/14 526/318.5 |
| 2015/0233614 A1 * | 8/2015 | Kindt | B01L 7/52 62/3.3 |
| 2017/0058843 A1 * | 3/2017 | Ham | F02D 41/22 |
| 2017/0355916 A1 * | 12/2017 | Troetsch-Schaller | C08F 4/34 |
| 2020/0017790 A1 * | 1/2020 | Weers | C09K 8/54 |

FOREIGN PATENT DOCUMENTS

| | | |
|---|---|---|
| GB | 1529051 | 10/1978 |
| JP | H10-274616 A | 10/1998 |
| WO | 2015/041672 A1 | 3/2015 |

OTHER PUBLICATIONS

International Preliminary Examination Report PCT/AT2016/000084 dated Sep. 7, 2017.

* cited by examiner

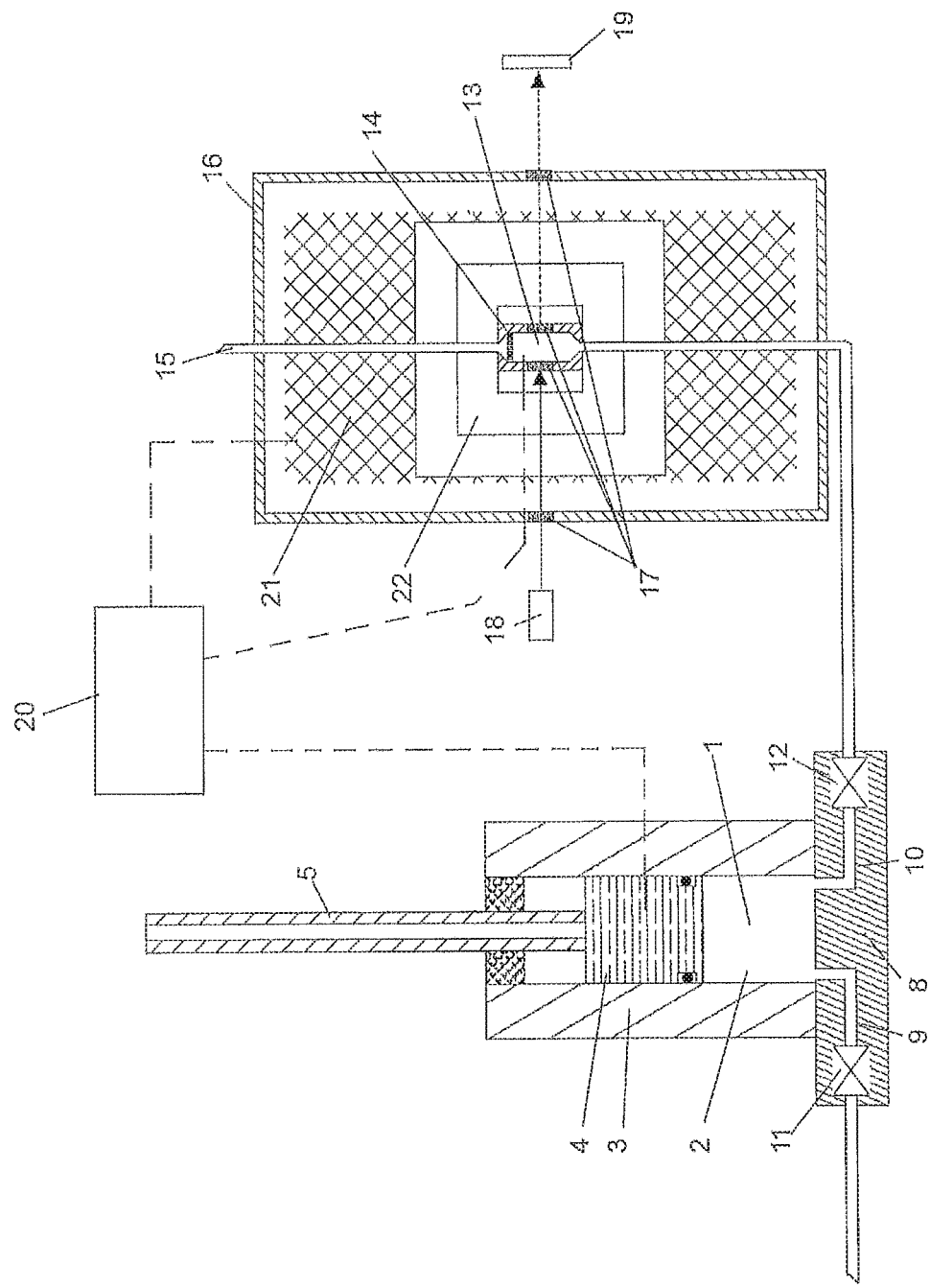

METHOD AND DEVICE FOR DETERMINING LOW TEMPERATURE PROPERTIES

CROSS-REFERENCE TO RELATED APPLICATIONS

This is the U.S. National Stage of PCT/AT2016/000084, filed Sep. 22, 2016, which in turn claims priority to: Austrian Patent Application No. A 636/2015, filed Sep. 29, 2015, the contents of each of these applications being incorporated herein by reference in their entireties.

The invention relates to a method for determining the low-temperature properties of a paraffin-containing fuel, in which the fuel is conducted from a storage chamber through a measuring cell provided with a sieve, the measuring cell is cooled by means of a cooling device, the temperature of the fuel in the measuring cell is measured, and a fluid pressure representing the flow resistance occurring on the sieve is measured, and the temperature occurring at a defined fluid pressure set point is determined and output as a result of the method.

The invention further relates to a device for carrying out such a method.

A method and a device of the initially defined kind are described in DD 120714. That method, in particular, serves to determine the cold filter plugging point of a paraffin-containing fuel.

At low temperatures, mineral oil distillates have the property of exhibiting poor flow behaviour and precipitating solid paraffin. If, for instance, a diesel fuel with a cloud point of 0° C. is maintained below 0° C. for an extended period of time, e.g. during a cold spell in winter, the paraffin will crystallize in the form of slab-like crystals causing the fuel to gel and preventing its passage through narrow lines and filters.

The cold filter plugging point temperature above which liquid mineral oil products can still be used without trouble is, thus, a suitable quality criterion for the usability of such substances in cold climate zones or during winter operation. It is known to perform the determination of the cold filter plugging point temperature in such a manner that a cooled sample of the fuel is pressed through a metal sieve of standard mesh size into a collecting vessel at regular temperature intervals (ASTM D6371). After the passage of the specified amount, the sample returns into the cooling cell under the influence of gravity. The cold filter plugging point temperature is considered to be achieved when the flow time in the filtering cycle exceeds a specified value (e.g. 60 seconds).

In another embodiment of the cold filter plugging point test (CFPP test), which is particularly recommended for European and additive-containing diesel fuels, the limit temperature at which a continuously cooled fuel sample lust does not pass a test sieve directly disposed in the cooling cell is determined in a sequence of regularly repeated suction and ventilation cycles.

While methods comprising suction and ventilation cycles operate discontinuously, a continuous method was proposed in DD 120714, in which the cooling and/or measuring cell equipped with a metal sieve of a defined mesh size is designed as a flow cell, through which the fuel to be tested flows continuously in one direction only. The flow resistance exhibited by the metal sieve for the product flow is determined by the pressure at the entrance to the measuring cell. The measuring cell is equipped with Peltier cooling batteries attached to its side faces, the cooling capacity of which is controlled as a function of the pressure measured value. Control is effected such that the preselected pressure corresponding to the temperature of the cold filter plugging point of the tested fuel adjusts after the deposition of a specific amount of paraffin crystals on the metal sieve. The sample temperature detected by a sensor constitutes the desired cold filter plugging point.

The method described in DD 120714 involves the drawback that exact measurements will only be achieved if a pregiven volume flow of the sample is set when the test device is put into operation, and is maintained equal during the whole process. The reason for this is that changes in the volume flow would falsify the results of the pressure measurement. Another disadvantage of the method according to DD 120714 resides in that a constant sample fluid flow is required such that a large sample volume is consumed.

The invention, therefore, aims to improve a method and a device of the initially defined kind to the effect that the defined volume flow can be adjusted and maintained in a simple manner and the consumed sample volume can be reduced.

To solve this object, the invention in a method of the initially mentioned kind provides that, for each pressure measurement, a defined sample amount of the fuel is abruptly delivered from the storage chamber in order to obtain a pressure pulse. In that a pressure pulse is used for measuring the fluid pressure, no constant flow volume of the fuel is required so as to enable a reduction of the volume of fuel required for the method. The desired volume flow results from the monitoring of the respectively ejected fuel amount and of the time over which the ejection takes place. At a short-term ejection of a small amount of fuel, the adjustment and monitoring of the volume flow are substantially easier to realize from a technological point of view than at constant fuel delivery.

In doing so, it is preferably operated such that the measurement of the fluid pressure during the cooling of the measuring cell is repeated at a number of different temperatures of the fuel in order to obtain a series of measured values, wherein, for each measurement, a defined, identical sample amount of the fuel is abruptly delivered from the storage chamber in order to obtain a pressure pulse. In that the measuring of the pressure during the cooling of the fuel is not effected continuously, but a series of measured values of pressure measurements performed at defined intervals is determined, no constant flow volume of the fuel is required so as to enable a reduction of the volume of the fuel required for the method. The observance of the required volume flow in this case is ensured in a simple manner in that, for each measurement, a defined, identical sample amount of the fuel is abruptly delivered from the storage chamber in order to obtain a pressure pulse. In a preferred manner, the ejection of a defined fuel amount is each ensured in that a delivery piston of a delivery device is displaced by a defined distance using a driving device, in particular a stepper motor. Alternatively, the defined fuel amount can also be supplied by a micropump.

The short-term ejection of the defined sample amount of fuel causes a pressure pulse downstream of the delivery device, or upstream of the sieve disposed in the measuring cell, due to the compressibility of the fuel. The pressure pulse is detected by the pressure sensor, wherein it is preferably operated such that the maximum of the fluid pressure occurring at a pressure pulse is each used as the fluid pressure measured value.

The flow resistance occurring on the sieve can basically be represented by various pressure measurements. Thus, for instance, a differential pressure of pressure values measured upstream and downstream of the sieve can be used as the fluid pressure representing the flow resistance. In a simple manner, it is preferably proceeded such that the fluid pressure prevailing upstream of the measuring cell is used as the fluid pressure representing the flow resistance occurring on the sieve.

The parameter to be determined by the method according to the invention, which characterizes the low-temperature property of the fuel, such as, in particular, the cold filter plugging point or CFPP, is basically determined in such a manner that at first a calibration is made, by which, using a fuel with a known temperature value of the parameter, in particular the cold filter plugging point, the fluid pressure measured at the known temperature value of the parameter of said fuel is determined. This pressure measured value is subsequently specified as the defined fluid pressure set point for the respective test device in regard to the respective parameter. With a nonlinear relationship between the cold filter plugging point and the fluid pressure, the calibration may be replaced by a correlation that takes into account said nonlinear relationship. As soon as the defined fluid pressure set point has been achieved when performing the test method using a fuel with an unknown parameter of the low-temperature property, the instantaneous temperature of the fuel in the measuring cell is determined and output as the sought temperature value of the parameter, e.g. the cold filter plugging point.

Bearing in mind the fact that, in the context of the method according to the invention, a series of measured values of discrete pressure measured values rather than a continuous pressure measuring signal is obtained, the desired parameter, such as the temperature of the cold filter plugging point, may be considered as determined when the instantaneous fluid pressure measured value exceeds the set point for the first time.

An increased accuracy will, however, be achieved according to a preferred mode of operation, if a characteristic curve of the fluid pressure as a function of the temperature is created from the series of measured values, and the temperature assigned to the defined fluid pressure set point in the characteristic curve is determined and output as a result of the method.

The method according to the invention is suitable not only for determining the cold filter plugging point (CFPP) of the fuel, but also for determining the pour point of the fuel. The pour point of the fuel is the temperature at which the latter still just flows upon cooling. For the definition of the flow property, the standards (DIN, ASTM) indicate different test methods.

The method according to the invention enables the determination of both the cold filter plugging point and the pour point in a single run. To this end, it is preferably provided that a first fluid pressure set point is specified, which is decisive for the cold filter plugging point, and that a second fluid pressure set point is specified, which is decisive for the pour point. As soon as the series of measured values has been obtained in a run, it is possible in the context of the evaluation of the series of measured values, or the characteristic curve created from the series of measured values, to determine the cold filter plugging point based on the first set point and the pour point based on the second set point.

The method may be performed such that the temperature of the fuel in the measuring cell is stepwisely reduced, particularly in steps of 1° C., and that a measurement of the fluid pressure is performed after each cooling step.

Alternatively, it is possible to continuously reduce the temperature of the fuel in the measuring cell and perform a measurement of the fluid pressure each during the passage of defined temperature steps. The continuous reduction of the temperature is preferred, because the method will be completed more rapidly.

Due to the configuration of the measuring cell as a flow cell, the cloud point and/or the freeze point of the fuel can also be determined in addition to cold filter plugging point and/or the pour point. This is preferably done in the measuring cell by an optical measuring method. The optical measuring method preferably comprises a transmitted light measurement.

The cloud point is also a low-temperature property of diesel fuel and heating oil, denoting the temperature (0° C.) at which a clear liquid product turns milky or cloudy due to the formation of paraffin crystals under defined test conditions.

If both the cold filter plugging point and/or the pour point and the cloud point are to be determined in a single run, it is preferably operated such that the fuel respectively present in the measuring cell is cooled, and the cloud point is determined during a first cooling step and the cold filter plugging point and/or the pour point are determined during a second cooling step.

In addition, it is also possible to determine the freeze point of the fuel in a simple manner. The freeze point together with the cloud point defines the melting interval. In this respect, it is preferably operated such that the fuel respectively present in the measuring cell is reheated after cooling, and the freeze point is determined during heating.

According to a further aspect of the invention, the object underlying the invention is achieved by a device for carrying out the method according to the invention, comprising a storage chamber for the fuel to be tested, a measuring cell in fluid-connection with the storage chamber, said measuring cell being designed as a flow cell and provided with a sieve, a delivery device for delivering fuel from the storage chamber through the measuring cell, a cooling device for cooling the measuring cell, a temperature sensor for measuring the temperature of the fuel in the measuring cell, a pressure sensor for measuring a fluid pressure representing the flow resistance occurring on the sieve, and a control unit to which the measured values of the temperature sensor and of the pressure sensor are fed, wherein the delivery device is configured to abruptly deliver a defined sample amount of the fuel from the storage chamber so as to obtain a pressure pulse.

The control unit may, for instance, be designed as a microcontroller.

The pressure pulse is preferably generated in that the delivery device comprises a piston delimiting the storage chamber and operable by a driving device. In particular, it is provided that the driving device comprises a stepper motor. Alternatively, the delivery device may comprise a micropump or other actuators such as piezo actuators.

It is preferably provided that the pressure sensor is arranged to measure the fluid pressure prevailing upstream of the measuring cell In a structurally particularly advantageous manner, the pressure sensor is integrated in the piston of the delivery device.

It is preferably provided that the control unit cooperates with the cooling device and with the delivery device to actuate the same as a function of the measured values of the temperature sensor and of the pressure sensor, and that the control unit is arranged to repeat the measurement of the fluid pressure during cooling of the measuring cell at a number of different temperatures of the fuel thus obtaining a series of measured values, and to abruptly deliver, for each measurement, a defined, identical sample amount of the fuel from the storage chamber.

In order to enable the processing of the pairs of measured values of the series of measured values, it is preferably provided that the control unit comprises an evaluation circuit to which the measured values of the pressure sensor and of the temperature sensor are fed, and which has optionally stored the series of measured values, said evaluation circuit determining, and outputting the same as a result of the method, the temperature occurring at a defined fluid pressure set point.

In a preferred manner, the maximum of the fluid pressure occurring at a pressure pulse is each used as the fluid pressure measured value in the evaluation circuit.

In this respect, the evaluation circuit is advantageously arranged to establish from the series of measured values a characteristic curve of the fluid pressure as a function of the temperature, and to determine, and output as a result of the method, the temperature assigned to the defined fluid pressure set point in the characteristic curve.

The control unit may cooperate with the cooling device for stepwisely reducing the temperature of the fuel. In the measuring cell, particularly in steps of 1° C., wherein a measurement of the fluid pressure is performed after each cooling step.

Alternatively, it is preferably provided that the control unit cooperates with the cooling device for continuously reducing the temperature of the fuel in the measuring cell, and that a measurement of the fluid pressure is each performed during the passage of defined temperature steps.

Another preferred further development provides that an optical measuring device for measuring the cloud point and/or the freeze point of the fuel is associated with the measuring cell. The optical measuring device, in particular, operates according to the transmitted light method and preferably comprises a light source disposed on one side of the measuring cell and a light sensor disposed on the opposite side of the measuring cell.

A cooling device with an adjustable cooling performance is preferably used for cooling the measuring cell. The cooling device preferably comprises at least one Peltier element. In this case, the measuring cell can be provided with Peltier elements either on one side or on two sides.

In the following, the invention will be explained in more detail by way of an exemplary embodiment schematically illustrated in the drawing. Therein, FIG. 1 illustrates a device according to the invention for determining the cloud point and the cold filter plugging point of a paraffin-containing fuel.

In FIG. 1, a storage chamber for the fuel to be tested is denoted by 1, accommodating a sample 2 of the fuel. The storage chamber 1 is formed in a hollow cylinder 3, which is closed on one side by an axially displaceable piston 4. The piston 4 comprises a piston rod 5 cooperating with a displacement drive (not illustrated) for the piston 4. The displacement drive may, for instance, be comprised of a stepper motor. On the side opposite the piston 4, the storage chamber 1 is closed by a valve block 8, in which the supply line 9 and the discharge line 10 are formed. The supply line 9 comprises a valve 11 and the discharge line comprises a valve 12.

With the valve opened, the discharge line 10 connects the storage chamber 1 to the measuring cell 13, which is designed as a flow cell and provided with a sieve 14. As soon as the piston has abruptly delivered a defined sample amount of the fuel from the storage chamber 1, the sample amount reaches the measuring cell 13 via line 10. The sample flows through the measuring cell 13, thus leaving the same on the side opposite the supply line via a discharge 15. A pressure value representing a flow resistance generated on the sieve 14 is determined by a pressure sensor, which in the present case is integrated in the piston 4. Alternatively, a pressure sensor disposed in the supply line 10 or at any other point upstream of the measuring cell 13 is also conceivable.

A cooling device is provided for cooling the measuring cell 13, the measuring cell 13 along with the cold side of the cooling device being thermally insulated as schematically indicated by 16.

It is further apparent from FIG. 1 that the measuring cell 13 comprises a glass window 17 each on two opposite sides. The thermal insulation 16 also comprises corresponding glass windows, or suitable optical passages 17, all optical elements 17 being in mutual alignment. On, one side of the measuring cell 13 a light source 18 such as a laser, and on the opposite side a photodetector 19, are disposed in such a manner that the light emitted from the light source 18 passes through the glass windows 17 and the measuring cell 13 and can be detected by the photodetector 19. Such a transmitted light method may be used to determine the cloud point of the sample.

Furthermore, a control unit 20 is provided, to which the measured values of a temperature sensor detecting the sample temperature within the measuring cell 13 and of the pressure sensor are fed and which controls the cooling performance of the cooling device. The cooling device for the measuring cell 13, for instance, comprises a cooling stage in contact with the measuring cell 13 and including a Peltier element 22. On the hot side of the Peltier element 22, a copper plate 21 equipped with a cooling body may be provided. In the copper plate may be formed bores or channels, through which a cooling fluid may be conducted.

The invention claimed is:

1. A method for determining a low temperature property of a paraffin-containing fuel, the method comprising:
    conducting the fuel from a storage chamber through a measuring cell provided with a sieve,
    cooling the measuring cell by means of a cooling device,
    a temperature measuring step comprising measuring a temperature of the fuel in the measuring cell to obtain a measured temperature,
    a pressure measuring step comprising:
        abruptly delivering a defined sample amount of fuel from the storage chamber to the measuring cells in order to obtain a pressure pulse of the fuel,
        measuring a fluid pressure of said pressure pulse to obtain a measured fluid pressure representing a flow resistance occurring on the sieve at said measured temperature, and
    determining if the measured fluid pressure corresponds to a fluid pressure set point, and, in the affirmative,
    outputting, as the low-temperature property of the fuel, the measured temperature as being assigned to the fluid pressure set point.

2. A method according to claim 1, wherein the pressure measuring step and the temperature measuring step occurs during the cooling of the measuring cell and are repeated at a number of different temperatures of the fuel in order to obtain a series of measured fluid pressures and a series of measured temperatures, and wherein, for each pressure measuring step, a defined, identical sample amount of the fuel is abruptly delivered from the storage chamber in order to obtain the pressure pulse.

3. A method according to claim 2, further comprising: establishing a characteristic curve of the fluid pressure as a function of the different temperatures from the series of measured fluid pressures and the series of measured temperatures, and determining a temperature assigned to the defined fluid pressure set point in the characteristic curve, and outputting, as the low-temperature property of the fuel, the determined temperature as being assigned to the fluid pressure set point.

4. A method according to claim 2, wherein measuring the fluid pressure of said pressure pulse to obtain the measured fluid pressure comprises determining a maximum of the fluid pressure occurring at a pressure pulse and using the maximum as the measured fluid pressure.

5. A method according to claim 1, wherein the measuring of the fluid pressure occurs upstream of the measuring cell and is used as the measured fluid pressure representing the flow resistance occurring on the sieve.

6. A method according to claim 1, wherein the determined low-temperature property of the fuel further comprises a cold filter plugging point and/or a pour point of the fuel and the method further comprises determining the cold filter plugging point and/or a pour point of the fuel as a result of the cooling of the measuring cell, and outputting the cold filter plugging point of the fuel and/or the pour point of the fuel.

7. A method according to claim 6, wherein a first fluid pressure set point is specified for determining the cold filter plugging point, and/or wherein a second fluid pressure set point is specified for determining the pour point.

8. A method according to claim 1, wherein the temperature of the fuel in the measuring cell is stepwisely reduced in steps of 1° C., and wherein the pressure measuring step is performed after each cooling step.

9. A method according to claim 1, wherein the temperature of the fuel in the measuring cell is continuously reduced, and wherein the pressure measuring step is each performed during passage of defined temperature steps.

10. A method according to claim 6, wherein the determined low-temperature property of the fuel further comprises a cloud point, a freeze point, or both, and the method further comprises determining the cloud point, the freeze point, or both, of the fuel in the measuring cell by an optical measuring method which comprises transmitting and measuring light through the measuring cell.

11. A method according to claim 10, comprising determining the cloud point, wherein the fuel respectively present in the measuring cell is cooled, and the cloud point is determined during a first cooling step and the cold filter plugging point, the pour point, or both, are determined during a second cooling step.

12. A method according to claim 11, comprising determining the freeze point, wherein the fuel respectively present in the measuring cell is reheated after cooling, and the freeze point is determined during heating.

13. A device for carrying out the method according to claim 1, the device comprising: the storage chamber for storing the fuel, the measuring cell in fluid-connection with the storage chamber, said measuring cell being designed as a flow cell and provided with the sieve, a delivery device for conducting the fuel from the storage chamber through the measuring cell, the cooling device for the cooling of the measuring cell, a temperature sensor for the measuring of the temperature of the fuel in the measuring cell, a pressure sensor for the measuring of the fluid pressure, and a control unit to which the measured temperature of the temperature sensor and the measured fluid pressure of the pressure sensor are fed,
wherein the delivery device is configured to abruptly deliver the defined sample amount of the fuel from the storage chamber so as to obtain the pressure pulse.

14. A device according to claim 13, wherein the delivery device comprises a piston delimiting the storage chamber and operable by a driving device.

15. A device according to claim 14, wherein the driving device comprises a stepper motor.

16. A device according to claim 13, wherein the delivery device comprises a micropump or a piezo pump.

17. A device according to claim 13, wherein the pressure sensor is arranged to measure the fluid pressure prevailing upstream of the measuring cell.

18. A device according to claim 14, wherein the pressure sensor is integrated in the piston of the delivery device.

19. A device according to claim 13, wherein the control unit cooperates with the cooling device and with the delivery device to actuate the cooling device and the delivery device as a function of the fed measured temperature of the temperature sensor and the fed measured fluid pressure of the pressure sensor, and that the control unit is arranged to repeat the measurement of the fluid pressure during the cooling of the measuring cell at a number of different temperatures of the fuel thus obtaining a series of measured pressure values, and to abruptly deliver, for each measurement, a defined, identical sample amount of the fuel from the storage chamber.

20. A device according to claim 19, wherein the control unit comprises an evaluation circuit to which the measured fluid pressure of the pressure sensor and the measured temperature of the temperature sensor are fed and which has stored the series of measured values, said evaluation circuit determining, and outputting, the temperature occurring at a defined fluid pressure set point.

21. A device according to claim 20, wherein a maximum of the fluid pressure occurring at a pressure pulse is determined and used as the fluid pressure measured value in the evaluation circuit.

22. A device according to claim 20, wherein the evaluation circuit is arranged to establish from the series of measured pressure values a characteristic curve of the fluid pressure as a function of the temperature, and to determine, and output, the temperature assigned to the defined fluid pressure set point in the characteristic curve.

23. A device according to claim 13, wherein the control unit cooperates with the cooling device for stepwisely reducing the temperature of the fuel in the measuring cell in steps of 1° C., wherein the measurement of the fluid pressure is performed after each cooling step.

24. A device according to claim 13, wherein the control unit cooperates with the cooling device for continuously reducing the temperature of the fuel in the measuring cell, and that the measurement of the fluid pressure is each performed during passage of defined temperature steps.

25. A device according to claim 13, wherein an optical measuring device for measuring a cloud point, a freeze point, or both, of the fuel is associated with the measuring cell, wherein the optical measuring device is configured to transmit and measure light through the measuring cell for the measuring of the cloud point, the freeze point, or both.

26. A device according to claim 25, wherein the optical measuring device comprises a light source disposed on one side of the measuring cell and a light sensor disposed on an opposite side of the measuring cell.

27. A method for determining a low-temperature property of a paraffin-containing fuel, the method comprising:
conducting the fuel from a storage chamber through a measuring cell provided with a sieve,
cooling the measuring cell by means of a cooling device,
a temperature measuring step comprising measuring a temperature of the fuel in the measuring cell to obtain a measured temperature,
a pressure measuring step comprising:
abruptly delivering a defined sample amount of the fuel from the storage chamber to the measuring cell in order to obtain a pressure pulse of the fuel,
measuring a fluid pressure of said pressure pulse to obtain a measured fluid pressure representing a flow resistance occurring on the sieve at said measured temperature,
repeating the pressure measuring step and the temperature measuring step at a number of different temperatures of the fuel in order to obtain a series of measured fluid pressures and a series of measured temperatures,
establishing a characteristic curve of the fluid pressure as a function of the different temperatures from the series of measured fluid pressures and the series of the measured temperatures, and determining a temperature assigned to a fluid pressure set point in the characteristic curve, and
outputting, as the low-temperature property of the fuel, the determined temperature as being assigned to the fluid pressure set point.

\* \* \* \* \*